(12) United States Patent  (10) Patent No.: US 6,589,956 B2
Lavielle et al.  (45) Date of Patent: Jul. 8, 2003

(54) BENZENESULPHONAMIDE COMPOUNDS

(75) Inventors: Gilbert Lavielle, La Celle Saint Cloud (FR); Bernard Cimetiere, Paris (FR); Tony Verbeuren, Vernouillet (FR); Serge Simonet, Conflans Sainte Honorine (FR); Christine Vayssettes-Courchay, Igny (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 10/195,031

(22) Filed: Jul. 12, 2002

(65) Prior Publication Data

US 2003/0109533 A1 Jun. 12, 2003

(30) Foreign Application Priority Data

Jul. 13, 2001 (FR) ............................................. 01 09338

(51) Int. Cl.⁷ .................... A61K 31/496; A61K 31/454; C07D 401/06; C07D 403/06; C07D 417/14
(52) U.S. Cl. ........................... 514/254.04; 514/254.09; 514/321; 514/323; 544/368; 544/373; 546/198; 546/201
(58) Field of Search ................................ 544/373, 368; 546/198, 201; 514/254.04, 254.09, 321, 323

(56) References Cited

U.S. PATENT DOCUMENTS 5,977,116 A * 11/1999 Castro Pineiro et al.
5,998,415 A * 12/1999 Chambers et al.
5,998,440 A * 12/1999 Castro Pineiro et al.

* cited by examiner

Primary Examiner—Emily Bernhardt
(74) Attorney, Agent, or Firm—The Firm of Hueschen and Sage

(57) ABSTRACT

A compound of formula (I):

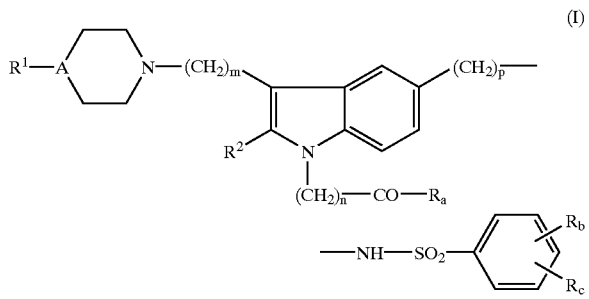

wherein:

$R_a$ represents a hydroxy, alkoxy, aryloxy or arylalkyloxy group,

A represents a CH group or a nitrogen atom, in which case $R^1$ is as defined in the description, or $R^1$—A together represent an oxygen atom or a group,

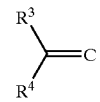

wherein $R^3$ and $R^4$ are as defined in the description, $R^2$ being a hydrogen atom or an alkyl group, $R_b$ and $R_c$, which may be identical or different, each represents a hydrogen atom, a halogen atom, an alkyl group, an alkoxy group, a hydroxy group or a trihaloalkyl group, n is an integer of from 2 to 6 inclusive, m and p are integers of from 0 to 6 inclusive, its enantiomers, diastereoisomers, and addition salts thereof with a pharmaceutically acceptable acid or base, and medicinal products containing the same which are useful as a $TXA_2$ receptor antagonist and 5-$HT_2$ receptor antagonist.

13 Claims, No Drawings

BENZENESULPHONAMIDE COMPOUNDS

SUMMARY OF THE INVENTION

The present invention relates to new benzenesulphonamide compounds, and to pharmaceutical compositions containing them.

The compounds of the present invention have a novel structure giving them a $TXA_2$ receptor antagonist and $5HT_2$ serotoninergic receptor antagonist character.

1. Description of the Prior Art

Compounds having a benzenesulphonamide chain have been described in Application EP 864 561 in relation to their NO-yielding character and their thromboxane $A_2$ ($TXA_2$) receptor antagonist character, as well as in Application EP 648 741 solely in relation to their $TXA_2$ receptor antagonist properties or WO 95 06046 as antagonists of receptors of $TXA_2$ and precursors thereof, prostaglandin $H_2$ ($PGH_2$).

2. Background of the Invention

Platelet aggregation and vasospasms play an essential role in the aetiology and development of atherothrombotic cardiovascular diseases. $TXA_2$, an arachidonic acid metabolite, and serotonin (5HT), a neurotransmitter, are both powerful vasoconstrictor agents, and are able to induce or reinforce platelet activation, resulting in the aggregation thereof. The vasoconstrictor and pro-aggregation actions of $TXA_2$ are effected through the intermediary of membrane receptors called TP receptors (Medicinal Research Reviews, 1991, 11, 5, p. 503) while those of serotonin are effected through the intermediary of $5HT_1$ or $5HT_2$ receptors (T.I.P.S., 1991, 121, p. 223). Research strategies pursued with the aim of finding agents that block the production and/or activation of $TXA_2$ have led to the development of selective TP receptor antagonists, of $TXA_2$-synthase inhibitors, or of mixed agents that exhibit both properties (Medicinal Research Reviews, ibid., T.I.P.S., 1991, 121, 158). Like $TXA_2$, serotonin acts by stimulating platelets and vascular constriction and its activity is found to be increased in atherothrombotic diseases.

The idea of compounds that oppose both the process that causes thromboxane to become active and the process that causes serotonin to become active is extremely useful for the clinician. Such products have the advantage of offering more complete protection both against the activation of platelets and against vasospasms. It will thus be possible for such products to be used in the treatment of pathologies associated with increased activity of $TXA_2$ and 5-HT especially in the treatment of atherothrombotic cardiovascular diseases, such as myocardial infarction, angina pectoris, cerebral vascular accidents, Raynaud's disease, and also asthma and bronchospasms, as well as migraine and venous diseases.

DETAILED DESCRIPTION OF THE INVENTION

The present invention relates to compounds of formula (I):

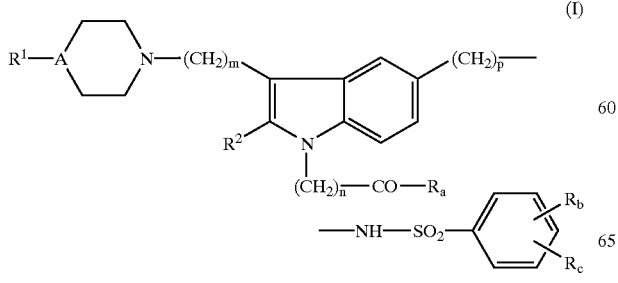

wherein:
$R_a$ represents a hydroxy, alkoxy, optionally substituted aryloxy or optionally substituted arylalkyloxy, amino, alkylamino, dialkylamino, optionally substituted arylamino or optionally substituted arylalkylamino group, A represents:
either a CH group, in which case $R^1$ represents a hydrogen atom or an alkyl, cycloalkyl, cycloalkylalkyl, optionally substituted aryl, optionally substituted arylcarbonyl, optionally substituted arylcarbonylalkyl, optionally substituted aryloxy, optionally substituted aryloxyalkyl, optionally substituted arylthio, optionally substituted arylthioalkyl, optionally substituted arylamino, optionally substituted arylalkylamino, optionally substituted heteroaryl, optionally substituted heteroarylalkyl, optionally substituted heteroarylcarbonyl, optionally substituted heteroarylcarbonylalkyl, optionally substituted heteroaryloxy, optionally substituted heteroaryloxyalkyl, optionally substituted heteroarylthio, optionally substituted heteroarylthioalkyl, optionally substituted heteroarylamino or optionally substituted heteroarylalkylamino group, or a nitrogen atom, in which case $R^1$ represents a hydrogen atom or an alkyl, cycloalkyl, cycloalkylalkyl, optionally substituted aryl, optionally substituted arylcarbonyl, optionally substituted arylcarbonylalkyl, optionally substituted arylsulphonyl, optionally substituted aryloxyalkyl, optionally substituted arylthioalkyl, optionally substituted heteroaryl, optionally substituted heteroarylalkyl, optionally substituted heteroarylcarbonyl, optionally substituted heteroarylcarbonylalkyl, optionally substituted heteroaryloxyalkyl, optionally substituted heteroarylsulphonyl or optionally substituted heteroarylthioalkyl group, or $R^1$—A together represent an oxygen atom or a group

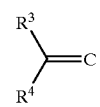

wherein $R^3$ and $R^4$, which may be identical or different, each represents a hydrogen atom, an optionally substituted aryl group, an alkyl group or an optionally substituted heteroaryl group, $R^2$ being a hydrogen atom or an alkyl group, $R_b$ and $R_c$, which may be identical or different, each represents a hydrogen atom, a halogen atom, an alkyl group, an alkoxy group, a hydroxy group or a trihaloalkyl group, n is an integer of from 2 to 6 inclusive, m and p are identical or different integers of from 0 to 6 inclusive, to their enantiomers and diastereoisomers, and also to addition salts thereof with a pharmaceutically acceptable acid or base, wherein:
the term "alkyl" denotes a linear or branched chain having from 1 to 6 carbon atoms,
the term "alkoxy" denotes a linear or branched alkyl-oxy group having from 1 to 6 carbon atoms, the term "trihaloalkyl" denotes a carbon chain having from 1 to 3 carbon atoms and from 1 to 3 identical or different halogen atoms, the term "cycloalkyl" denotes a saturated cyclic group having from 3 to 8 carbon atoms, the term "aryl" denotes a phenyl or naphthyl group, the term "heteroaryl" denotes an aromatic monocyclic group, or a bicyclic group in which at least one of the rings is aromatic, having from 5 to 11 ring members and from 1 to 5 hetero atoms selected from nitrogen, oxygen and sulphur, the term "substituted" relating to aryl, arylcarbonyl, arylcarbonylalkyl, aryloxy, aryloxyalkyl, arylthio, arylthioalkyl, arylamino, arylalkylamino, heteroaryl, heteroarylalkyl, heteroarylcarbonyl, heteroarylcarbonylalkyl, heteroaryloxy, heteroaryloxyalkyl, heteroarylthio, heteroarylthioalkyl, heteroarylamino, and heteroarylalkylamino, arylsulphonyl, arylsulphonylalkyl, heteroarylsulphonyl and heteroarylsulphonylalkyl, denotes that the groups in question are substituted in the aromatic moiety by one or two identical or different substituents selected from halogen atoms and alkyl groups, alkoxy groups, hydroxy groups, cyano groups, nitro groups, amino groups (optionally substituted by one or two alkyl groups) and groups $C(O)R_d$, $R_d$ representing a group selected from hydroxy, alkoxy and amino, wherein the heteroaryl and heteroarylalkyl groups may also be substituted by an oxo group in the non-aromatic moiety of the heteroaryl.

Preferred compounds of the invention are those wherein, taken together or separately, the value of the substituent m is 2, the value of n is 2, the value of p is 2, the substituent $R_a$ represents a hydroxy group and the substituent $R^2$ represents a hydrogen atom or a methyl group.

An especially advantageous embodiment of the invention relates to compounds of formula (I) wherein m, n and p are each 2, $R_a$ represents a hydroxy group, $R^2$ represents a hydrogen atom or a methyl group, $R_b$ represents a halogen atom, $R_c$ represents a hydrogen atom, and A represents a nitrogen atom in which case $R^1$ represents a hydrogen atom or an alkyl, cycloalkyl, optionally substituted aryl, optionally substituted arylcarbonyl or optionally substituted heteroaryl group, or A represents a CH group in which case $R^1$ represents a hydrogen atom or an alkyl, cycloalkyl, optionally substituted aryl, optionally substituted arylcarbonyl or optionally substituted heteroaryl group, or $R^1$—A together represent an oxygen atom or a group $R^3R^4C=C$ wherein $R^3$ and $R^4$ represent an optionally substituted aryl group.

More especially, preferred compounds of formula (I) are those wherein m, n and p are each 2, $R_a$ represents a hydroxy group, $R^2$ represents a hydrogen atom or a methyl group, $R_b$ represents a halogen atom in the para position of the phenyl ring, $R_c$ represents a hydrogen atom and either A represents a nitrogen atom, in which case $R^1$ represents a phenyl group optionally substituted by a halogen atom, or a heteroaryl group having 9 ring members that contains one or two hetero atoms selected from nitrogen, oxygen and sulphur and is optionally substituted by a halogen atom or A represents CH group, in which case $R^1$ represents a phenyl group optionally substituted by a halogen atom, a phenylcarbonyl group optionally substituted by a halogen atom, or a heteroaryl group having 9 ring members that contains one or two hetero atoms selected from nitrogen, oxygen and sulphur and is optionally substituted by a halogen atom, or $R^1$—A together represent a group $R^3R^4C=C$ wherein $R^3$ and $R^4$ each represents a phenyl group optionally substituted by a halogen atom.

Advantageously, the invention relates to compounds of formula (I) wherein the optionally substituted heteroaryl group $R^1$ is a benzisoxazolyl group optionally substituted by a halogen atom, a benzothienyl group optionally substituted by a halogen atom, or a benzisothiazolyl group optionally substituted by a halogen atom.

Amongst the preferred compounds of the invention, 3-[3-{2-[4-(1,2-benzisothiazol-3-yl)-1-piperazinyl]ethyl}-5-(2-{[(4-chlorophenyl)sulphonyl]amino}ethyl)-1H-indol-1-yl] propanoic acid may be mentioned.

The present invention relates also to a process for the preparation of compounds of formula (I), which is characterised in that there is used as starting material a compound of formula (II):

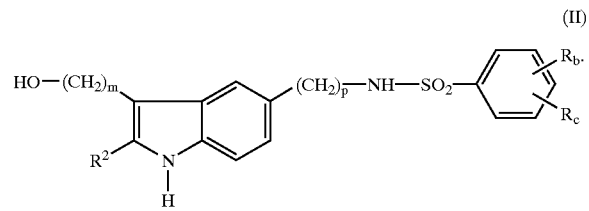

wherein $R^2$, $R_b$, $R_c$, m and p are as defined for formula (I), which is halogenated to yield a compound of formula (III):

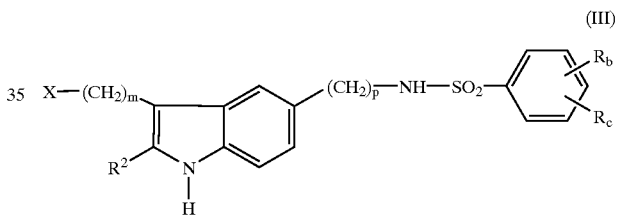

wherein $R^2$, $R_b$, $R_c$, m and p are as defined for formula (I) and X represents a halogen atom, the halogen atom of which is replaced by an amino group of formula:

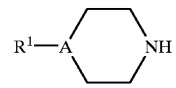

to yield a compound of formula (IV):

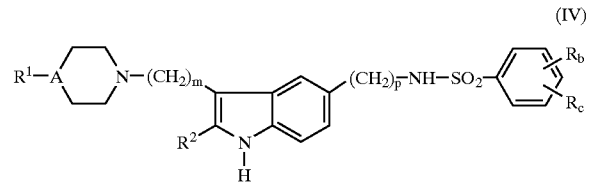

wherein $R^1$, A, $R^2$, $R_b$, $R_c$, m and p are as defined for formula (I), which is subjected to condensation on the indole nitrogen with acrylonitrile, followed by hydrolysis of the nitrile compound in alkaline medium to yield a compound of formula (I/a), a particular case of formula (I):

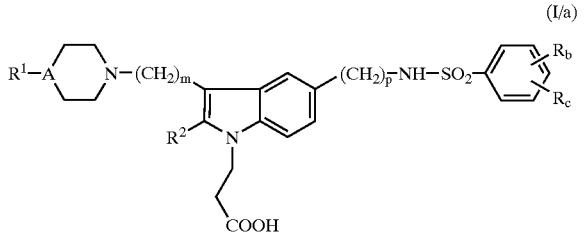

wherein R¹, A, R², $R_b$, $R_c$, m and p are as defined for formula (I), the carboxylic acid function of which is optionally converted by reduction into aldehyde, for reaction with an appropriate phosphorus ylid, and which, after catalytic reduction, yields (I/b), a particular case of formula (I):

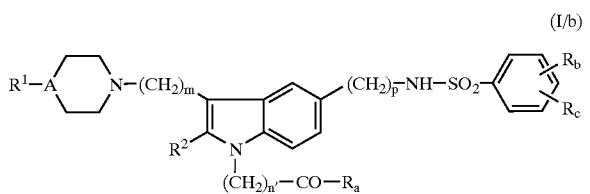

wherein R¹, A, R², $R_a$, $R_b$, $R_c$, m and p are as defined for formula (I) and n' is an integer of from 4 to 6, which compounds of formula (I/b) may be subjected to hydrolysis of the ester function in acidic or basic medium, according to the reactive groups in the molecule, to yield a compound of formula (I/c):

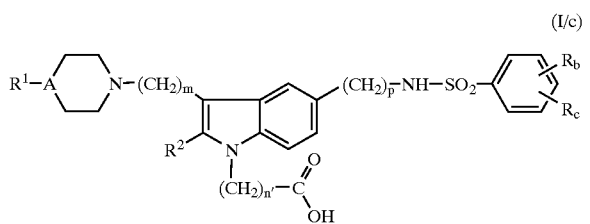

a particular case of the compounds of formula (I) wherein R¹, R², $R_b$, $R_c$, m and p are as defined for formula (I) and n' is an integer of from 4 to 6, which compounds (I/a), (I/b) and (I/c) constitute the totality of the compounds of formula (I) and:

- may, if desired, be purified according to a conventional purification technique,
- are optionally separated into their stereoisomers according to a conventional separation technique,
- are, if desired, converted into their addition salts with a pharmaceutically acceptable acid or base, it being understood that, at any point considered appropriate during the course of the process described above, the carboxylic acid function may be esterified or the carboxylic ester function may be hydrolysed to the corresponding acid, which may be converted again to a different ester as required by the synthesis.

The present invention relates also to pharmaceutical compositions comprising as active ingredient at least one compound of formula (I), alone or in combination with one or more pharmaceutically acceptable, inert, non-toxic excipients or carriers.

Amongst the pharmaceutical compositions according to the invention there may be mentioned more especially those which are suitable for oral, parenteral or nasal administration, tablets or dragees, sublingual tablets, gelatin capsules, lozenges, suppositories, creams, ointments, dermal gels, etc.

The useful dosage varies in accordance with the age and weight of the patient, the nature and the severity of the disorder and also the administration route, which may be oral, nasal, rectal or parenteral. Generally, the unit dosage ranges from 0.1 mg to 500 mg for a treatment of from 1 to 3 administrations per 24 hours.

The following Examples illustrate the invention and do not limit it in any way. The structures of the described compounds have been confirmed by customary spectroscopic and spectrometric techniques.

The starting materials employed are known products or products prepared according to known procedures.

Preparation A

4-Chloro-N-{2-[3-(2-hydroxyethyl)-1H-indol-5yl] ethyl}-benzenesulphonamide

Step a: N-[2-(4-Aminophenyl)ethyl]-4-chlorobenzenesulphonamide 47.5 ml of triethylamine and then, in portions, 72 g of 4-chlorobenzenesulphonyl chloride, are added at ambient temperature to a solution of 46.5 g (340 mmol) of 4-(2-aminoethyl)aniline in a liter of dichloromethane. The mixture is then stirred for one night and subsequently filtered. The solid obtained is washed with water and dried using a dessicator to yield the expected product.

Step b: 4-Chloro-N-[2-(4-hydrazinophenyl)ethyl] benzenesulphonamide Hydrate

A solution of 11.5 g of sodium nitrite in 40 ml of water is added at −10° C. to a suspension of 20 g (64 mmol) of the product described in the above Step in 140 ml of concentrated hydrochloric acid. After stirring for 10 minutes at −10° C., a solution of 200 g of tin dichloride in 260 ml of concentrated hydrochloric acid is added. The suspension is stirred for 3 hours at ambient temperature. The solid obtained is filtered off and taken up in 800 ml of methanol. Insoluble material is filtered off and the volume of methanol is reduced by evaporation to a volume of 400 ml. The expected product is isolated by crystallisation.

Step c: 4-Chloro-N-[2-[3-(2-hydroxyethyl)-]H-indol-5-yl] ethylybenzenesulphonamide A solution of 5.8 ml (45 mmol) of 2-ethoxytetrahydrofuran in 240 ml of ethanol is added at 60° C. over a period of 20 minutes to a solution of 15 g (41 mmol) of the product described in the above Step in a mixture of 145 ml of ethanol and 15 ml of water. The mixture is heated at reflux for 4 hours. After removal of the solvent by evaporation and purification on a silica column using a 95/5/0.5 dichloromethane/methanol/ammonium hydroxide mixture as eluant, the title product is obtained Preparation B 4-Chloro-N-{2-[3-(2-hydroxyethyl)-2-methyl-1H-indol-5-yl]ethyl}-benzenesulphonamide The expected product is obtained according to the procedures described in Preparation A, with the replacement of 2-ethoxytetrahydrofuran with 5-hydroxy-2-pentanone in Step c.

Preparation C

4-Chloro-N-{2-[3-(3-hydroxypropyl)-1H-indol-5-yl] ethyl}benzenesulphonamide

Step a: N-[2-(4-Aminophenyl)ethyl]-4-chlorobenzene- sulphonamide

The expected product is obtained according.to the procedure described in Preparation A, Step a.

Step b: N-[2-(4-Amino-3-iodophenyl)ethyl]-4-chlorobenzenesulphonamide 2.08 g of calcium carbonate and 5.56 g of benzyltrimethylammonium dichloroiodate are added at ambient temperature to a solution of 5 g (16 mmol) of the above-synthesised product in 100 ml of methanol and 50 ml of dichloromethane. After stirring for 3 hours, the suspension is filtered and the filtrate is evaporated. The solid obtained is taken up in dichloromethane, and the solution is washed with aqueous 10% sodium bisulphate solution and then with water, and subsequently dried over magnesium sulphate. Evaporation of the solvent yields the expected product.

Step c: 4-Chloro-N-{2-[3-(3-hydroxypropyl)-1H-indol-5-yl]ethyl}benzenesulphonamide Preparation of trimethylsilyl 5-(trimethylsilyl)-4-pentynyl ether.

300 ml of a solution of 1.6N n-butyllithium in hexane are added at −35° C. to a solution of 20 g (237 mmol) of 4-pentyn-1-ol in 250 ml of THF. After stirring for 30 minutes at −20° C., 62 ml (486 mmol) of trimethylsilyl chloride are added. After increasing again to ambient temperature and stirring for 2 hours, 600 ml of ether and 600 ml of pentane are added, followed by an aqueous 1% sodium carbonate solution. After decanting, drying the organic phase over magnesium sulphate and removing the solvents by evaporation, the silylated compound is isolated.

There are suspended, in 100 ml of DMF, 5 g (11.5 mmol) of trimethylsilyl 5-(trimethylsilyl)-4-pentynyl ether prepared above, 2.6 g (11.5 mmol) of the product described in Preparation C, Step b, 6 g of sodium carbonate and 100 mg of palladium acetate. The reaction mixture is heated at 110° C. for 4 hours. The DMF is then evaporated off and the mixture is taken up in dichloromethane. The organic phase is washed with water and dried over magnesium sulphate and the solvent is evaporated off. The black oil obtained is taken up in 50 ml of ethanol and then treated with 5 ml of 1N hydrochloric acid. After 2 hours at ambient temperature, the ethanol is evaporated off. The oil is taken up in dichloromethane, and the organic phase is washed with water, dried over magnesium sulphate and evaporated to yield the expected product.

EXAMPLE 1

3-(5(2-{[(4-Chlorophenyl)sulphonyl]amino}ethyl)-3-{2-[4-(4-fluorobenzoyl)-1-piperidyl]ethyl}-1H-indol-1-yl)propanoic Acid Step a: N-{2-[3-(2-Bromoethyl)-1H-indol-5-yl]ethyl}-4-chlorobenzenesulphonamide 3.3 g (12.6 mmol) of triphenylphosphine, and then 4.2 g (12.6 mmol) of carbon tetrabromide in 30 ml of acetonitrile, are added at ambient temperature to a suspension of 4 g (10.5 mmol) of the product obtained in Preparation A, Step c, in 60 ml of acetonitrile. The mixture is stirred for 2 hours and then the solvent is evaporated off. After chromatography on a silica column using a 20/80 ethyl acetate/cyclohexane mixture as eluant, the title product is obtained.

Step b: 4-Chloro-N-[2-(3-{2-[4-(4-fluorobenzoyl)-1-piperidyl]ethyl}-1H-indol-5-yl)ethyl]benzenesulphonamide 11 g (2.9 mmol) of potassium carbonate are added to a solution of 3.2 g (0.72 mmol) of the product obtained in above Step in 100 ml of DMF. The mixture is heated at 70° C. under nitrogen for 1 hour. The DMF is then evaporated off and the resulting oil is taken up in dichloromethane. The organic phase obtained is washed with water, dried over magnesium sulphate and evaporated. The residue is purified by chromatography on a silica column using a 47/3 dichloromethane/methanol mixture as eluant.

Step c: 4-Chloro-N-[2-(1-(2-cyanoethyl)-3-{2-[4-(4-fluorobenzoyl)-1-piperidyl]-ethyl}-1H-indol-5-yl)ethyl]benzenesulphonamide 190 mg of 60% sodium hydride are added at ambient temperature to a solution of 2.4 g (4.22 mmol) of the product obtained in the above Step in 40 ml of DMF. When the evolution of gas has ceased, a solution of 450 mg of acrylonitrile in 10 ml of DMF is added at ambient temperature. After stirring for 1 hour, 50 ml of a saturated aqueous sodium chloride solution are added. After extraction with ethyl acetate, drying over magnesium sulphate and removal of the solvents by evaporation, the expected product is purified by chromatography on a silica column using a 98/2 dichloromethane/methanol mixture as eluant.

Step d: 3-(5-(2-{[(4-Chlorophenyl)sulphonyl]amino}ethyl)-3-{2-[4-(4-fluorobenzoyl)-1-piperidyl]ethyl}-1H-indol-1-yl)propanoic Acid 20 ml of an aqueous 10% potassium hydroxide solution are added to a solution of 1.4 g (2.25 mmol) of the product obtained in the above Step in 100 ml of isopropanol. After 4 hours at reflux, the isopropanol is evaporated off and water is added. The addition of acetic acid until a pH of 5 is obtained causes the separation of an oil, which is purified by chromatography on a silica column, using a 95/5/0.5 dichloromethane/methanol/acetic acid mixture as eluant, to yield the expected product.

| Elemental microanalysis: | | | | | |
|---|---|---|---|---|---|
| | C | H | N | Halogen | S |
| % Found | 61.13 | 5.45 | 6.39 | 5.77 | 4.49 |
| % Calculated | 61.92 | 5.51 | 6.56 | 5.54 | 5.01 |

EXAMPLE 2

3-(5-(2-{[(4-Chlorophenyl)sulphonyl]amino}ethyl)-3-{2-[4-(4-fluorophenyl)-1-piperazinyl]ethyl}-1H-indol-1-yl)propanoic Acid The expected product is obtained according to the procedure described in Example 1, with the replacement of 4-(4-fluorobenzoyl)piperidinium tosylate with 1-(4-fluorophenyl) piperazine in Step b.

| Elemental microanalysis: | | | | | |
|---|---|---|---|---|---|
| | C | H | N | Halogen | S |
| % Found | 60.17 | 5.51 | 8.77 | 6.05 | 5.1 |
| % Calculated | 60.73 | 5.59 | 9.14 | 5.78 | 5.23 |

EXAMPLE 3

3-[3-(2-{4-[bis(4-Fluorophenyl)methylene]-1-piperidyl}ethyl)-5-(2-{[(4-chlorophenyl)sulphonyl]amino}ethyl)-1H-indol-1-yl]propanoic Acid The expected product is obtained according to the procedure described in Example 1, with the replacement 4-(4-fluorobenzoyl)piperidinium tosylate with 4-[bis(4-fluorophenyl)-methylene]piperidine in Step b.

| Elemental microanalysis: | | | | | |
|---|---|---|---|---|---|
| | C | H | N | Cl | S |
| % Found | 64.90 | 5.34 | 5.79 | 5.03 | 4.36 |
| % Calculated | 65.22 | 5.33 | 5.85 | 4.94 | 4.46 |

EXAMPLE 4

3-(5-(2-{[(4-Chlorophenyl)sulphonyl]amino}ethyl)-3-{2-[4-(6-fluoro-1,2-benzisoxazol-3-yl)-1-piperidyl]ethyl}-1H-indol-1-yl)-propanoic Acid The expected product is obtained according to the procedure described in Example 1, with the replacement of 4-(4-fluorobenzoyl)piperidinium tosylate with 6-fluoro-3-(4-piperidyl)-1,2-benzisoxazole hydrochloride in Step b.

| Elemental microanalysis: | | | | | |
|---|---|---|---|---|---|
| | C | H | N | Cl | S |
| % Found | 60.62 | 5.17 | 8.44 | 5.72 | 4.90 |
| % Calculated | 60.68 | 5.25 | 8.58 | 5.43 | 4.91 |

EXAMPLE 5

3-(5-(2-{[(4-Chlorophenyl)sulphonyl]amino}ethyl)-3-{2-[4-(6-fluoro-1,2-benzisothiazol-3-yl)-1-piperidyl]ethyl}-1H-indol-1-yl)-propanoic Acid The expected product is obtained according to the procedure described in Example 1, with the replacement of 4-(4-fluorobenzoyl)piperidinium tosylate with 6-fluoro-3-(4-piperidyl)-1,2-benzisothiazole hydrochloride in Step b.

| Elemental microanalysis: | | | | | |
|---|---|---|---|---|---|
| | C | H | N | Halogen | S |
| % Found | 58.75 | 5.12 | 8.14 | 5.49 | 9.25 |
| % Calculated | 59.23 | 5.12 | 8.37 | 5.30 | 9.58 |

EXAMPLE 6

3-[3-{2-[4-(1,2-Benzisothiazol-3-yl)-1-piperazinyl]ethyl}-5-(2-{[(4-chlorophenyl)sulphonyl]amino}ethyl)-1H-indol-1-yl]propanoic Acid The expected product is obtained according to the procedure described in Example 1, with the replacement of 4-(4-fluorobenzoyl)piperidinium tosylate with 3-(1-piperazinyl)-1,2-benzisothiazole hydrochloride in Step b.

| Elemental microanalysis: | | | | | |
|---|---|---|---|---|---|
| | C | H | N | Halogen | S |
| % Found | 58.28 | 5.20 | 10.29 | 5.65 | 9.88 |
| % Calculated | 58.93 | 5.25 | 10.74 | 5.44 | 9.83 |

EXAMPLE 7

3-(5(2-{[(4-Chlorophenyl)sulphonyl]amino}ethyl)-3-{2-[4-(6-fluoro-1-benzothien-2-yl)-1-piperidyl]ethyl}-1H-indol-1-yl)-propanoic Acid The expected product is obtained according to the procedure described in Example 1, with the replacement of 4-(4-fluorobenzoyl)piperidinium tosylate with 4-(6-fluoro-1-benzothien-2-yl)piperidine hydrochloride in Step b.

| Elemental microanalysis: | | | | | |
|---|---|---|---|---|---|
| | C | H | N | Cl | S |
| % Found | 64.90 | 5.34 | 5.79 | 5.03 | 4.36 |
| % Calculated | 65.22 | 5.33 | 5.85 | 4.94 | 4.46 |

EXAMPLE 8

3-(5-(2-{[(4-Chlorophenyl)sulphonyl]amino}ethyl)-3-{2-[4-(6-fluoro-1,2-benzisoxazol-3-yl)-1-piperidyl]ethyl}-2-methyl-1H-indol-1-yl)propanoic Acid Step a: N-{2-[3-(2-Bromoethyl)-2-methyl-1H-indol-5-yl]ethyl}-4-chlorobenzenesulphonamide The expected product is obtained by bromination of the reagent synthesised in Preparation B, Step c, and according to the procedure described in Example 1, Step a.

Step b: 4-Chloro-N-[2-(3-{2-[4-(6-fluoro-1,2-benzisoxazol-3-yl)-1-piperidyl]-ethyl}-2-methyl-1H-indol-5-yl)ethyl]benzenesulphonamide The expected product is obtained starting from the reagent prepared in the above Step and according to the procedure described in Example 4, Step b.

Step c: 4-Chloro-N-[2-(1-(2-cyanoethyl)-3-{2-[4-(6-fluoro-1,2-benzisoxazol-3-yl)-1-piperidyl]ethyl}-2-methyl-1H-indol-5-yl)ethyl]benzenesulphonamide The expected product is obtained starting from the reagent prepared in the above Step and according to the procedure described in Example 1, Step c.

Step d: 3-(5-(2-{[(4-Chlorophenyl)sulphonyl]amino}ethyl)-3-{2-[4-(6-fluoro-1,2-benzisoxazol-3-yl)-1-piperidy]ethyl}-2-methyl-1H-indol-1-yl)propanoic Acid The expected product is obtained starting from the reagent prepared above and according to the procedure described in Example 1, Step d.

| Elemental microanalysis: | | | | | |
|---|---|---|---|---|---|
| | C | H | N | Cl | S |
| % Found | 61.31 | 5.43 | 8.47 | 5.64 | 4.51 |
| % Calculated | 61.21 | 5.44 | 8.40 | 5.31 | 4.81 |

EXAMPLE 9

3-(5-(2-{[(4-Chlorophenyl)sulphonyl]amino}ethyl)-3-{3-[4-(4-fluorobenzoyl)-1-piperidyl]propyl}-1H-indol-1-yl)propanoic Acid Step a: N-{2-[3-(3-Bromopropyl)-1H-indol-5-yl]ethyl}-4-chlorobenzenesulphonamide The expected product is obtained starting from the reagent prepared in Preparation C, Step c, and according to the procedure described in Example 1, Step a.

Step b: 4-Chloro-N-[2-(3-{3-[4-(4-fluorobenzoyl)-1-piperidyl]propyl}-1H-indol-5-yl)ethyl]benzenesulphonamide The expected product is obtained starting from the reagent prepared in the above Step and according to the procedure described in Example 1, Step b.

Step c: 4-Chloro-N-[2-(1-(2-cyanoethyl)-3-{3-[4-(4-fluorobenzoyl)-1-piperidyl]-propyl}-1H-indol-5-yl)ethyl]benzenesulphonamide The expected product is obtained starting from the reagent prepared in the above Step and according to the procedure described in Example 1, Step c.

Step d: 3-(5-(2-{[(4-Chlorophenyl)sulphonyl]amino}ethyl)-3-{3-[4-(4-fluorobenzoyl)-1-piperidyl]propyl}-1H-indol-1-yl)propanoic Acid The expected product is obtained starting from the reagent prepared in the above Step and according to the procedure described in Example 1, Step d.

| Elemental microanalysis: | | | | | |
|---|---|---|---|---|---|
| | C | H | N | Cl | S |
| % Found | 62.14 | 5.59 | 6.37 | 6.12 | 4.19 |
| % Calculated | 62.42 | 5.70 | 6.42 | 5.42 | 4.90 |

EXAMPLE 10

3-(5-(2-{[(4-Chlorophenyl)sulphonyl]amino}ethyl)-3-{3-[4-(4-fluorophenyl)-1-piperazinyl]propyl}-1H-indol-1-yl)propanoic Acid Hydrochloride The expected product is obtained according to the procedure described in Example 9, with the replacement 4-(4-fluorobenzoyl)piperidinium tosylate with 1-(4-fluorophenyl)-piperazine in Step b.

| Elemental microanalysis: | | | | | |
|---|---|---|---|---|---|
| | C | H | N | Halogen | S |
| % Found | 57.80 | 5.89 | 8.07 | 4.82 | 4.59 |
| % Calculated | 57.92 | 5.62 | 8.44 | 5.34 | 4.83 |

PHARMACOLOGICAL STUDY

EXAMPLE A

Platelet Aggregation in Man

Venous blood is obtained from human volunteers who have not taken aspirin for at least 14 days prior to the experiment. The blood is removed over sodium citrate (0.109 M) (1 vol. of citrate over 9 vol. of blood). Platelet-rich plasma (PRP) is obtained by centrifugation (20° C.) at 200 g for 10 minutes. The number of platelets is on average. 250000 PL/mm$^3$. The PRP is stored at room temperature until the test and is used within 2 hours of having been taken. The TXA$_2$ agonist U46619 is used at a concentration of 1 μM and 5-hydroxytryptamine is used at a concentration of 10 μM, the latter in the presence of 0.3 μM adenosine diphosphate and 1 μM adrenalin.

The compounds of the invention inhibit platelet aggregation induced by the TXA$_2$ agonist as well as that produced by 5-hydroxytryptamine. By way of example, the IC$_{50}$ values of the compound of Example 6 in the two experiments are 1.5 μM and 3.0 μM respectively.

The values indicate that the compounds of the invention are powerful platelet anti-aggregants, which act in a balanced manner on the two activation routes, that of TXA$_2$ and that of serotonin.

EXAMPLE B

Pharmaceutical Composition

Formulation for the preparation of 1000 tablets each containing a dose of 5 mg:

compound of Example 4 5 g
hydroxypropyl methylcellulose 2 g
wheat starch 10 g
lactose 100 g
magnesium stearate 3 g

We claim:

1. A compound of formula (I):

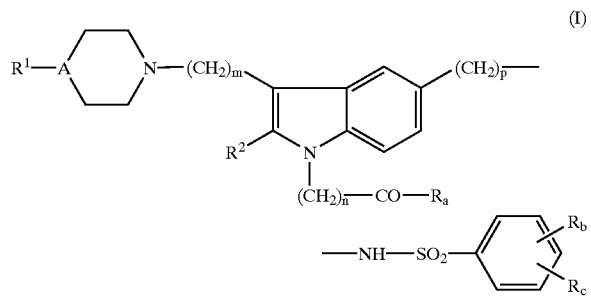

wherein:

R$_a$ represents a hydroxy, alkoxy, optionally substituted aryloxy or optionally substituted arylalkyloxy, amino, alkylamino, dialkylamino, optionally substituted arylamino or optionally substituted arylalkylamino group, A represents:
either a CH group, in which case R$^1$ represents a hydrogen atom or an alkyl, cycloalkyl, cycloalkylalkyl, optionally substituted aryl, optionally substituted arylcarbonyl, optionally substituted arylcarbonylalkyl, optionally substituted aryloxy, optionally substituted aryloxyalkyl, optionally substituted arylthio, optionally substituted arylthioalkyl, optionally substituted arylamino, optionally substituted arylalkylamino, optionally substituted heteroaryl, optionally substituted heteroarylalkyl, optionally substituted heteroarylcarbonyl, optionally substituted heteroarylcarbonylalkyl, optionally substituted heteroaryloxy, optionally substituted heteroaryloxyalkyl, optionally substituted heteroarylthio, optionally substituted heteroarylthioalkyl, optionally substituted heteroarylamino or optionally substituted heteroarylalkylamino group, or a nitrogen atom, in which case R$^1$ represents a hydrogen atom or an alkyl, cycloalkyl, cycloalkylalkyl, optionally substituted aryl, optionally substituted arylcarbonyl, optionally substituted arylcarbonylalkyl, optionally substituted arylsulphonyl, optionally substituted aryloxyalkyl, optionally substituted arylthioalkyl, optionally substituted heteroaryl, optionally substituted heteroarylalkyl, optionally substituted heteroarylcarbonyl, optionally substituted heteroarylcarbonylalkyl, optionally substituted heteroaryloxyalkyl, optionally substituted heteroarylsulphonyl or optionally substituted heteroarylthioalkyl group, or R$^1$—A together represent an oxygen atom or a group

wherein R$^3$ and R$^4$, which may be identical or different, each represents a hydrogen atom, an optionally substituted aryl group, an alkyl group or an optionally substituted heteroaryl group, R$^2$ being a hydrogen atom or an alkyl group, $R_b$ and $R_c$, which may be identical or different, each represents a hydrogen atom, a halogen atom, an alkyl group, an alkoxy group, a hydroxy group or a trihaloalkyl group, n is an integer of from 2 to 6 inclusive m and p are identical or different integers of from 0 to 6 inclusive, its enantiomers and diastereoisomers, and addition salts thereof with a pharmaceutically acceptable acid or base, wherein:

the term "alkyl" denotes a linear or branched chain having from 1 to 6 carbon atoms, the term "alkoxy" denotes a linear or branched alkyl-oxy group having from 1 to 6 carbon atoms, the term "trihaloalkyl" denotes a carbon chain having from 1 to 3 carbon atoms and from 1 to 3 identical or different halogen atoms, the term "cycloalkyl" denotes a saturated cyclic group having from 3 to 8 carbon atoms, the term "aryl" denotes a phenyl or naphthyl group, the term "heteroaryl" is selected from benzisoxazolyl, benzothienyl, and benzisothiazolyl, the term "substituted" relating to aryl, arylcarbonyl, arylcarbonylalkyl, aryloxy, aryloxyalkyl, arylthio, arylthioalkyl, arylamino, arylalkylamino, heteroaryl, heteroarylalkyl, heteroarylcarbonyl, heteroarylcarbonylalkyl, heteroaryloxy, heteroaryloxyalkyl, heteroarylthio, heteroarylthioalkyl, heteroarylamino, and heteroarylalkylamino, arylsulphonyl, arylsulphonylalkyl, heteroarylsulphonyl and heteroarylsulphonylalkyl, wherein the "substituted" aromatic groups are substituted in the aromatic moiety by one or two identical or different substituents selected from halogen atoms, alkyl groups, alkoxy groups, hydroxy groups, cyano groups, nitro groups, amino groups (optionally substituted by one or two alkyl groups) and group $C(O)R_d$, wherein $R_d$ represents a group selected from hydroxy, alkoxy and amino, and wherein the heteroaryl and heteroarylalkyl groups may also be substituted by an oxo group in the non-aromatic moiety of the heteroaryl.

2. A compound of claim 1, wherein m is 2.

3. A compound of claim 1, wherein n is 2.

4. A compound of claim 1, wherein p is 2.

5. A compound of claim 1, wherein $R_a$ represents a hydroxy group.

6. A compound of claim 1, wherein $R^2$ represents a hydrogen atom or a methyl group.

7. A compound of claim 1, wherein m, n and p are each 2, $R_a$ represents a hydroxy group, $R^2$ represents a hydrogen atom or a methyl group, $R_b$ represents a halogen atom, $R_c$ represents a hydrogen atom, and A represents a nitrogen atom, in which case $R^1$ represents a hydrogen atom or an alkyl, cycloalkyl, optionally substituted aryl, optionally substituted arylcarbonyl or optionally substituted heteroaryl group, or A represents a CH group in which case $R^1$ represents a hydrogen atom or an alkyl, cycloalkyl, optionally substituted aryl, optionally substituted arylcarbonyl, or optionally substituted heteroaryl group, or $R^1$—A together represent an oxygen atom or a group $R^3R^4C{=}C$ wherein $R^3$ and $R^4$ represent an optionally substituted aryl group.

8. A compound of claim 1, wherein m, n and p are each 2, $R_a$ represents a hydroxy group, $R^2$ represents a hydrogen atom or a methyl group, $R_b$ represents a halogen atom in the para position of the phenyl ring, $R_c$ represents a hydrogen atom and either A represents a nitrogen atom, in which case $R^1$ represents a phenyl group optionally substituted by a halogen atom, or a heteroaryl group having 9 ring members that contains one or two hetero atoms selected from nitrogen, oxygen and sulphur, which may optionally be substituted by a halogen atom, or A represents a CH group, in which case $R^1$ represents a phenyl group optionally substituted by a halogen atom, a phenylcarbonyl group optionally substituted by a halogen atom, or a heteroaryl group having 9 ring members that contains one or two hetero atoms selected from nitrogen, oxygen and sulphur, which group may optionally be substituted by a halogen atom, or $R^1$—A together represent a group $R^3R^4C{=}C$, wherein $R^3$ and $R^4$ each represents a phenyl group, optionally substituted by a halogen atom.

9. A compound of claim 1, wherein the optionally substituted heteroaryl group $R^1$ is a benzisoxazolyl group optionally substituted by a halogen atom, a benzothienyl group optionally substituted by a halogen atom, or a benzisothiazolyl group optionally substituted by a halogen atom.

10. A compound of claim 1, which is 3-[3-{2-[4-(1,2-benzisothiazol-3-yl)-1-piperazinyl]ethyl}-5-(2-{[(4-chlorophenyl)sulphonyl]amino}ethyl)-1H-indol-1-yl]propanoic acid.

11. A pharmaceutical composition useful as a $TXA_2$ receptor antagonist and a 5-$HT_2$ receptor antagonist comprising as active principle an effective amount of a compound as claimed in claim 1, together with one or more pharmaceutically acceptable excipients or vehicles.

12. A method for treating an animal or human living body afflicted with an atherothrombotic cardiovascular condition, comprising the step of administering to the living body an amount of a $TXA_2$ receptor antagonist and a 5-$HT_2$ receptor antagonist compound of claim 1 which is effective for alleviation of the condition.

13. A method for treating an animal or human living body afflicted with myocardial infarction, angina pectoris, cerebral vascular accidents, Raynaud's disease, or also asthma, bronchospasms, migraine and venous diseases, comprising the step of administering to the living body an amount of a $TXA_2$ receptor antagonist and a 5-$HT_2$ receptor antagonist compound of claim 1 which is effective for alleviation of the condition.

* * * * *

UNITED STATES PATENT AND TRADEMARK OFFICE
CERTIFICATE OF CORRECTION

PATENT NO. : 6,589,956 B2  Page 1 of 1
DATED : July 8, 2003
INVENTOR(S) : Gilbert Lavielle et al.

It is certified that error appears in the above-identified patent and that said Letters Patent is hereby corrected as shown below:

Title page,
Item [57], ABSTRACT, Formula (I)

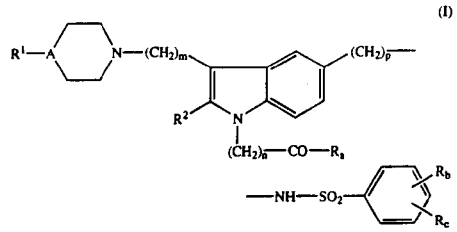

should be Formula (I)

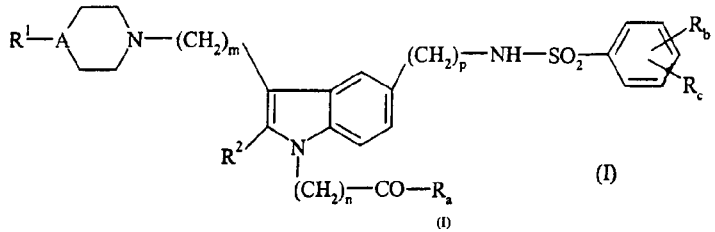

Column 12,
Line 5, Formula (I)

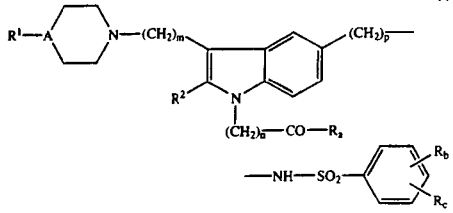

should be Formula (I)

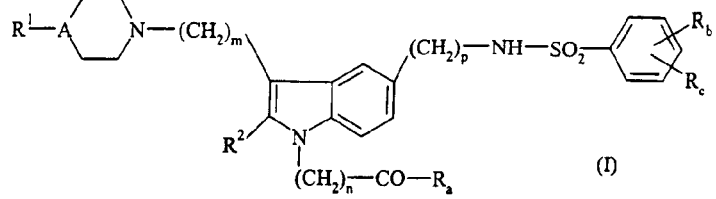

Signed and Sealed this

Twenty-first Day of October, 2003

JAMES E. ROGAN
*Director of the United States Patent and Trademark Office*